United States Patent
Chang et al.

(10) Patent No.: US 9,579,021 B2
(45) Date of Patent: *Feb. 28, 2017

(54) WEARABLE ELECTRONIC DEVICE

(71) Applicant: Rooti Labs Limited, Cayman (KY)

(72) Inventors: Ming-Shiung Chang, New Taipei (TW); Ko-Mai Li, New Taipei (TW); Shu-Chen Chuang, New Taipei (TW)

(73) Assignee: Rooti Labs Limited, Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/714,861

(22) Filed: May 18, 2015

(65) Prior Publication Data
US 2016/0073881 A1    Mar. 17, 2016

(30) Foreign Application Priority Data
Sep. 12, 2014 (CN) .......................... 2014 1 0463521

(51) Int. Cl.
*A61B 5/00* (2006.01)
*A61B 5/024* (2006.01)
*A61B 5/0245* (2006.01)

(52) U.S. Cl.
CPC .......... *A61B 5/0015* (2013.01); *A61B 5/6838* (2013.01); *A61B 5/002* (2013.01); *A61B 5/0245* (2013.01); *A61B 5/02438* (2013.01); *A61B 2560/0443* (2013.01)

(58) Field of Classification Search
CPC ..... A61B 5/0015; A61B 5/6838; A61B 5/002; A61B 5/02438; A61B 5/0245
See application file for complete search history.

(56) References Cited

U.S. PATENT DOCUMENTS

2015/0094558 A1* 4/2015 Russell .................. A61B 5/688
600/391

\* cited by examiner

*Primary Examiner* — Leon Flores
(74) *Attorney, Agent, or Firm* — Zhigang Ma

(57) ABSTRACT

A wearable electronic device includes a signal capturing assembly and a holder. The holder includes a case defining a receiving slot configured for receiving the signal capturing assembly, a first connecting electrode, and a second connecting electrode. The first and second connecting electrodes protrude from a bottom surface of the case and are electronically connected to the signal capturing assembly. The first and second connecting electrodes detect vital signs of a user and transmit the detected vital signs to the signal capturing assembly.

21 Claims, 6 Drawing Sheets

WEARABLE ELECTRONIC DEVICE

CROSS-REFERENCE TO RELATED APPLICATION

This application is related to co-pending U.S. patent application Ser. No. 14/715,863, entitled "WEARABLE ELECTRONIC DEVICE", and invented by Chang et al. The related application has the same assignee as the present application and has been concurrently filed herewith. The above-identified application is incorporated herein by reference.

FIELD

The subject matter herein generally relates to wearable electronic devices, and particularly to a wearable electronic device can be worn on clothes of a user.

BACKGROUND

Electronic devices are commonplace throughout most of the world today. Advancements in integrated circuit technology have enabled the development of miniature electronic devices that are wearable such as smart watches, smart eyeglasses, electronic rings, etc.

BRIEF DESCRIPTION OF THE DRAWINGS

Many aspects of the present disclosure can be better understood with reference to the drawings. The components in the drawings are not necessarily drawn to scale, the emphasis instead being placed upon clearly illustrating the principles of the disclosure. Moreover, in the drawings, like reference numerals designate corresponding parts throughout the views.

DETAILED DESCRIPTION

Figure 1:
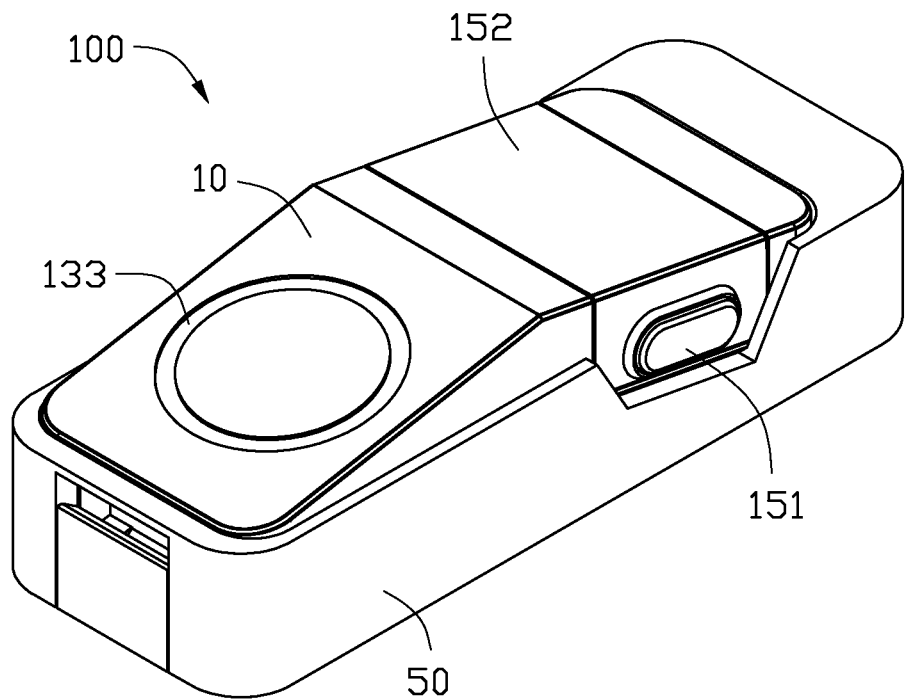
FIG. 1 is an isometric view of a wearable electronic device, according to an exemplary embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape, or other feature that the term modifies, such that the component need not be exact. For example, "substantially cylindrical" means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

FIG. 1 is an isometric view of a wearable electronic device 100, according to an exemplary embodiment. The wearable electronic device 100 includes a signal capturing assembly 10, a holder 50, and an accessory 70. The signal capturing assembly 10 is configured for monitoring and processing vital signs of a user (such as heart rate, temperature, pulse, blood pressure and so on). The holder 50 is detachably connected to the signal capturing assembly 10 and configured to be worn by the user. The accessory 70 is detachably connected to the signal capturing assembly 10 and configured for charging the signal capturing assembly 10 and transmitting the processed vital signs from the signal capturing assembly 10 to other electronic devices such as a mobile phone, or a computer.

Figure 2:
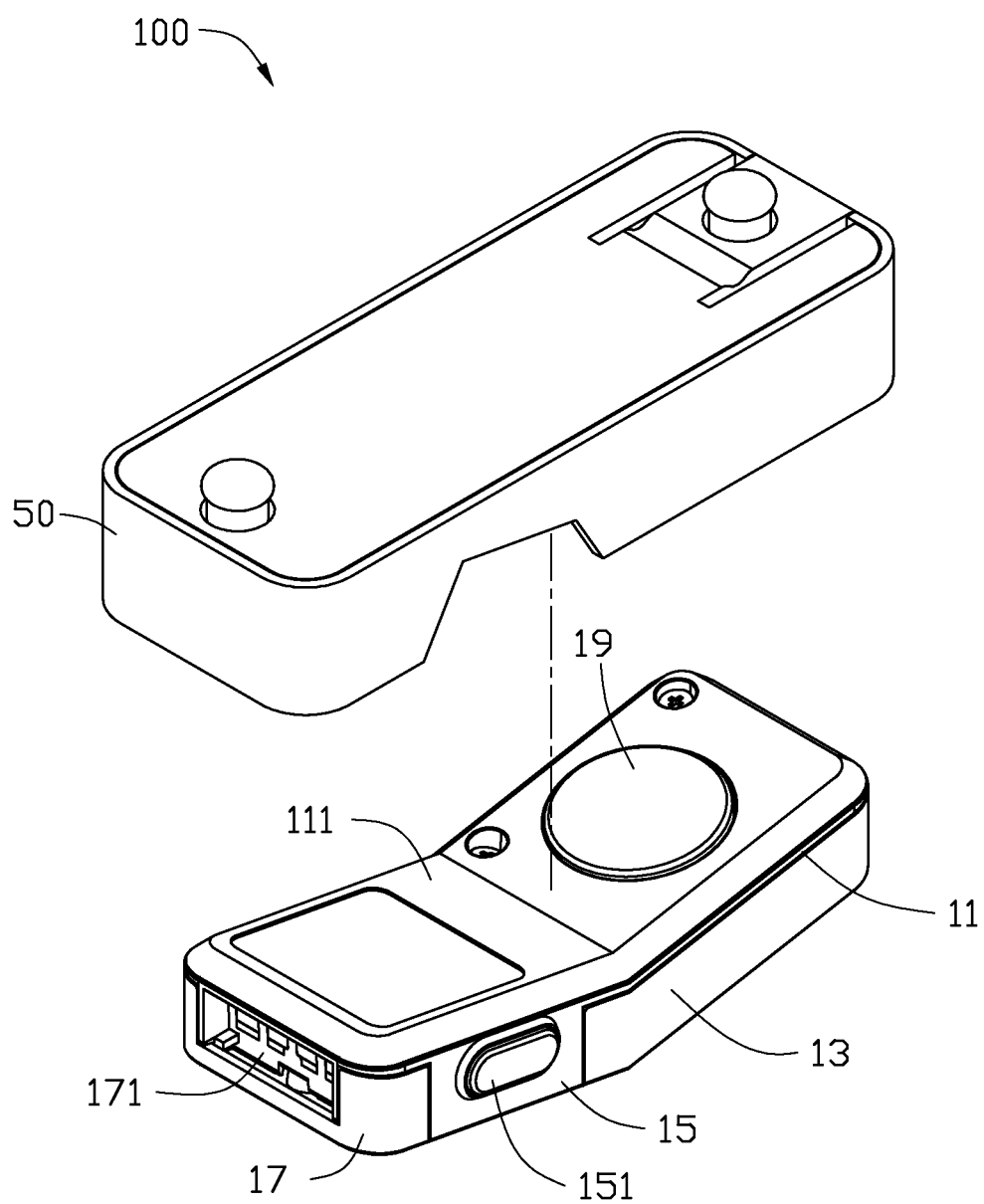
FIG. 2 is an exploded view of a signal capturing assembly and a holder of the wearable electronic device of FIG. 1.
Figure 6:
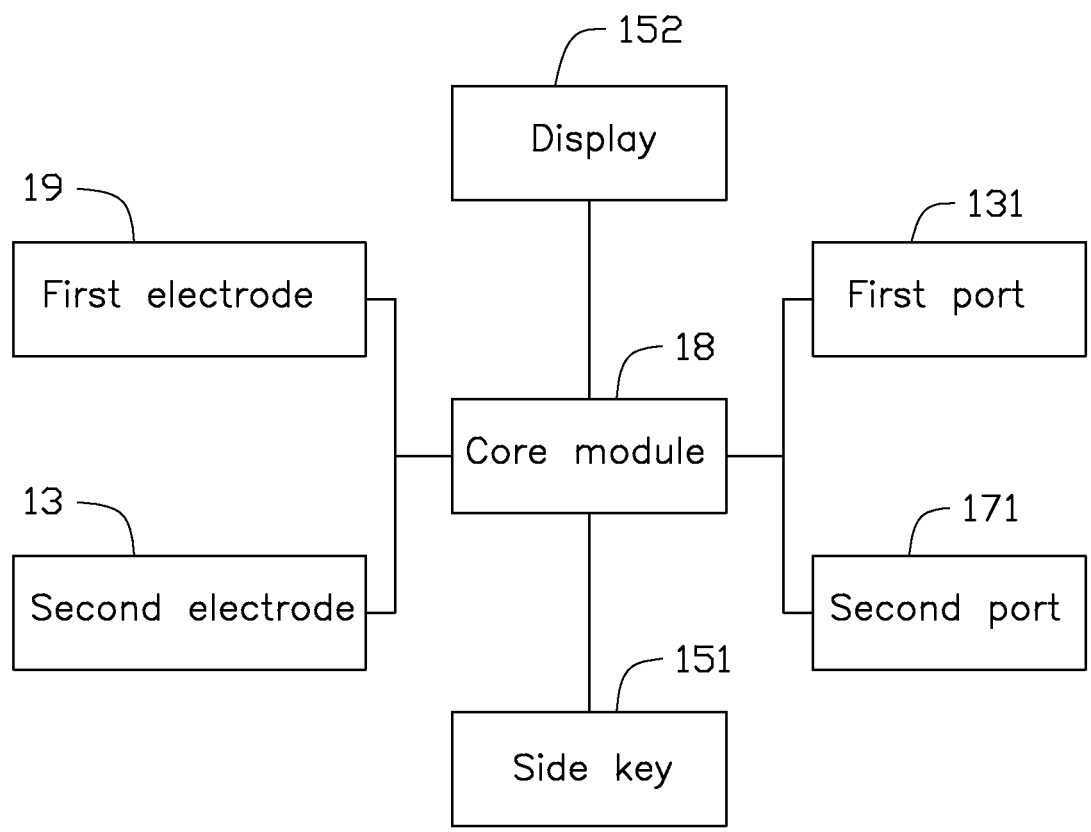
FIG. 6 is a block diagram of the wearable electronic device of FIG. 1.

FIG. 2 illustrates that the signal capturing assembly 10 includes a base 11, a first cover 13, a second cover 15, a third cover 17, a first electrode 19, and a core module 18 (shown in FIG. 6).

The base 11 is a substantially curved plate having a first curved portion in a middle portion of the base 11. In this exemplary embodiment, an obtuse angle is formed at the first curved portion so that the signal capturing assembly 10 can fit the wrists of a user. A sealing layer 111 is arranged on an outer surface of the base 11. The sealing layer 111 is made of rubber. The first, second, and third covers 13, 15, 17 cover the base 11 to define a receiving chamber to accommodate the core module 18; wherein the first and third covers 13, 17 are made of conductive material, and the second housing 15 is made of plastic material. The first cover 13 has a second curved portion corresponding to the first curved portion. The first cover 13 serves as a second electrode of the signal capturing assembly 10 and is electronically connected to the core module 18.

A ring-shaped label 133 is positioned on a surface of the first cover 13 and configured for labeling a contact position of the first cover 13. The first electrode 19 is extended through a bottom surface of the base 11. FIG. 6 illustrates that the first electrode 19 is electrically connected to the core module 18. When the label 133 is pressed by the user, a loop is formed between the first electrode 19 and the second electrode so that the first electrode 19 detects the vital signs of the user and transmits the detected vital signs to the core module 18. The core module 18 realizes the vital signs detecting and processing functions of the signal capturing assembly 10. In addition, the core module 18 can also support a vibrating promoting function of the signal capturing assembly 10. In other embodiment, a finger of the left hand and a finger of the right hand of the user are respectively attached to the first electrode 19 and the second electrode to formed the loop between the first electrode 19 and the second electrode.

A first port 131 is positioned at an end of the first cover 13. The first port 131 has a latching structure (e.g. a latching slot) configured for detachably connecting to the wearable assemblies 20. A side key 151 is arranged at one side of the second cover 15. The side key 151 is electronically connected to the core module 18 and configured for powering on/off the signal capturing assembly 10 or setting working parameters of the core module 18. A display 152 is arranged on a surface of the second cover 15. The display 152 is electronically connected to the core module 18 and configured for displaying a health of the user based on the vital signs, the working parameters of the core module 18, and so on. A second port 171 similar to the first port 131 is positioned at an end of the third cover 17 and is configured for detachably connecting to the wearable assemblies 20 or the accessory 70.

Figure 3:
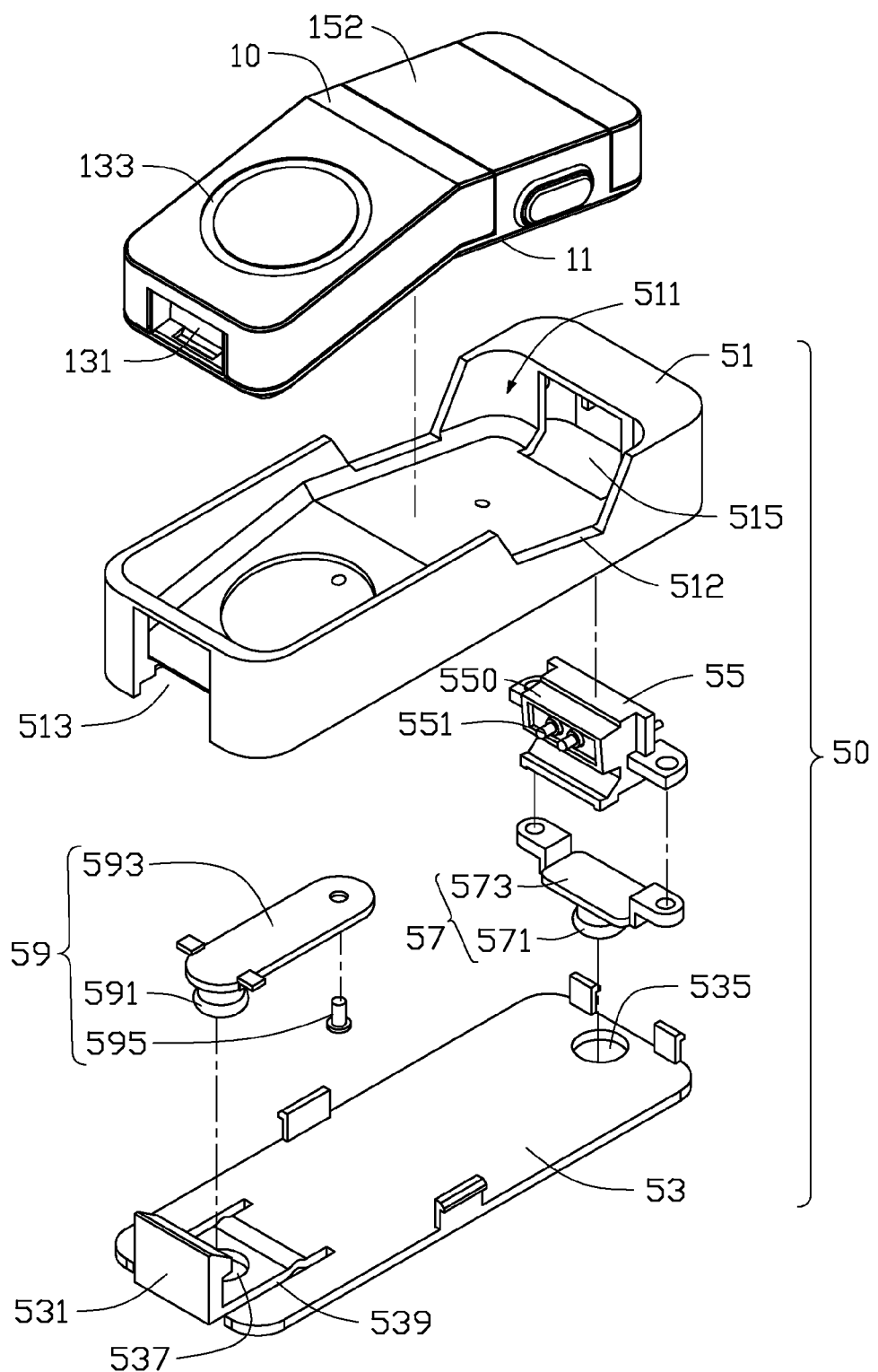
FIG. 3 is an exploded view of the wearable electronic device of FIG. 1.
Figure 4:
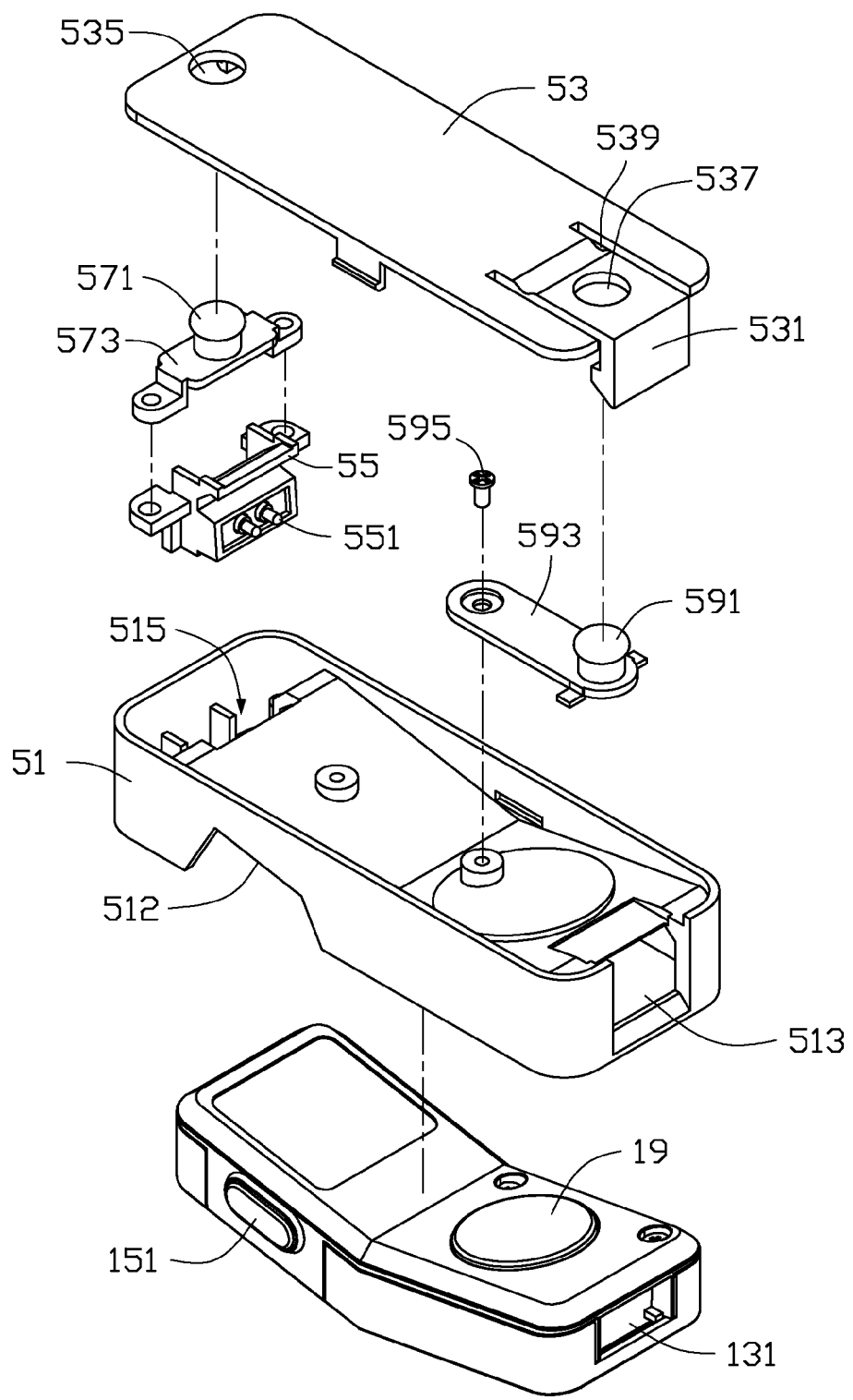
FIG. 4 is similar to FIG. 3, but shown from another angle.

FIGS. 3 and 4 illustrate that the holder 50 includes a case 51, a latching plate 53, a convertor 55, a first connecting electrode 57, and a second connecting electrode 59.

A receiving slot 511 is defined in the case 51 and configured for receiving the signal capturing assembly 10. Two opposite cutouts 512 are defined in two opposite sidewalls of the case 512. The side key 151 is exposed from one of the cutouts 512. The cutouts 512 are configured for conveniently operating the side key 151 and removing the signal capturing assembly 10 from the receiving slot 511. A through hole 513 is defined in an end of the case 512. A latching slot 515 is defined in another end of the case 51 opposite to the through hole 513 and communicating with the receiving slot 511.

The latching plate 53 is corresponding to a bottom surface of the case 51 and secured on the bottom surface of the case 51. Two opposite slits 539 are defined at an end of the latching plate 53. A portion of the latching plate 53 between the slits 539 is perpendicularly extended for a distance to form a substantially L-shaped hook 531. The hook 531 is exposed from the through hole 513 facing the receiving slot 511 and configured for latching to the first port 131. A first mounting hole 535 and a second mounting hole 537 are defined at two ends of the latching plate 53 and configured for exposing the first connecting electrode 57 and the second connecting electrode 59.

The convertor 55 is received in the latching slot 515 and configured for connecting to the second port 171. The convertor 55 includes a protruding block 550. Two contacting rods 551 protrude from the protruding block 550 and are configured for electrically connecting to core module 18. The convertor 55 is assembled into the latching slot 515 with the protruding block 550 facing the receiving slot 511. When the signal capturing assembly 10 is received in the receiving slot 511, the protruding block 550 engages with the second port 171 thereby detachably connecting the second port 171 to the holder 50. The contacting rods 551 can be electronically connected to the core module 18 via the second port 171.

The first connecting electrode 57 and the second connecting electrode 59 are extended from the bottom surface of the case 51. In the embodiment, the first connecting electrode 57 includes a first protrusion 571 and a securing member 573. The first protrusion 571 is arranged at one side of the securing member 573 and extending from the bottom surface of the case 51 through the first mounting hole 535. The securing member 573 is secured on the case 51, for example, by a screw orderly fastened from the convertor 55 and the securing member 573.

The second connecting electrode 59 includes a second protrusion 591, a positioning member 593, and a fastener 595 (e.g. a screw). The second protrusion 591 is arranged at an end of the positioning member 593 and protrudes from the bottom surface of the case 51 through the second mounting hole 537. The fastener 595 is extended through another end of the positioning member 593 opposite to the protrusion 591 and latches the positioning member 593 to the case 51. The first protrusion 571 and the second protrusion 591 are configured for integrating the holder 50 with the clothes of the user so that the signal capturing assembly 10 received in the holder 50 can be worn with the clothes of the user.

The first connecting electrode 57 and the second connecting electrode 59 are electronically connected to the contacting rods 551. The first connecting electrode 57 and the second connecting electrode 59 detect the vital signs of the user and transmit the detected vital signs to the core module 18 via the contacting rods 551.

Figure 5:
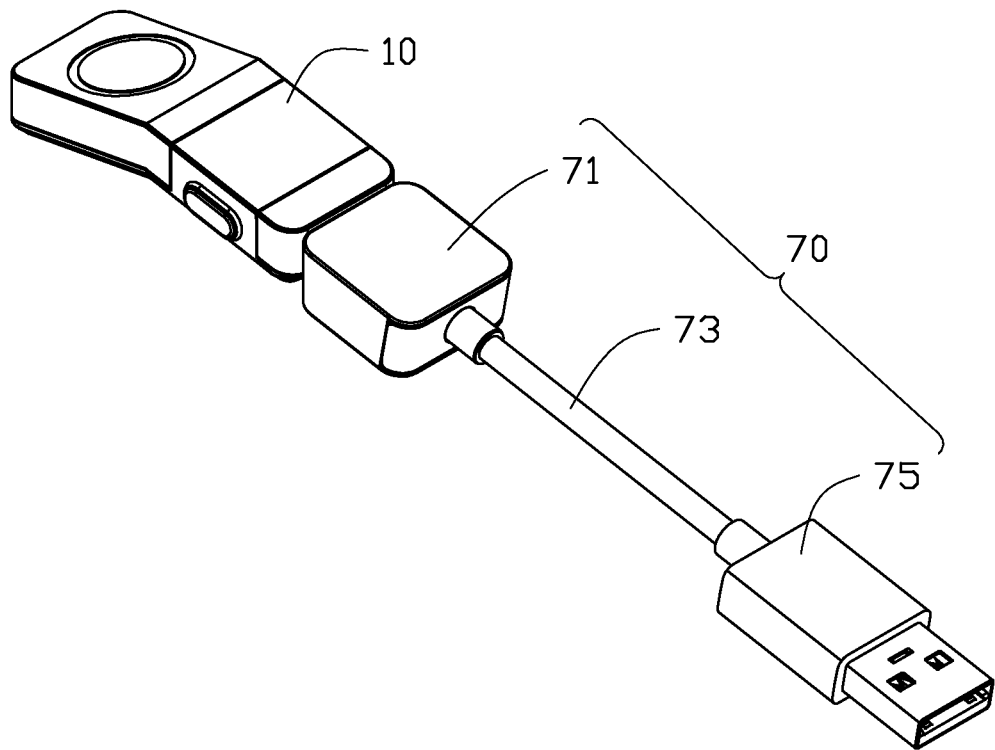
FIG. 5 is an isometric view of an accessory of the wearable electronic device of FIG. 1.

FIG. 5 illustrates that the accessory 70 includes a first connecting portion 71, a cable 73, and a second connecting portion 75. The first and second connecting portions 71, 75 are connected to two opposite ends of the cable 73. A rib 711 is protruded from an end of the first connecting portion 71 opposite to the second connecting portion 75. The rib 711 is configured for latching the first connecting portion 71 to the second port 171. The first connecting portion 71 can be electronically connected to the core module 18 via the second port 171 so that the signal capturing assembly 10 can be charged or connected to other electronic device by the accessory 70.

In this exemplary embodiment, the convertor 55 and the accessory 70 share the second port 171. To charge the signal capturing assembly 10 or connect the signal capturing assembly 10 to the other electronic device, the signal capturing assembly 10 is removed from the holder 50 and connected to the second port 171.

The wearable electronic device 100 can be worn with the clothes of the user via the holder 50 rather than being worn on the wrist, neck and head of users.

It is to be understood, however, that even through numerous characteristics and advantages of the present disclosure have been set forth in the foregoing description, together with details of assembly and function, the disclosure is illustrative only, and changes may be made in the details, especially in the matters of shape, size, and arrangement of parts within the principles of the disclosure to the full extent indicated by the broad general meaning of the terms in which the appended claims are expressed.

What is claimed is:

1. A wearable electronic device comprising:
   a signal capturing assembly, wherein the signal capturing assembly defines a first port at an end of the signal capturing assembly; and
   a holder, the holder comprising:
      a case defining a receiving slot configured for receiving the signal capturing assembly;
      a first connecting electrode;
      a second connecting electrode, the first and second connecting electrodes protruding from a bottom surface of the case and being electronically connected to the signal capturing assembly, the first and second connecting electrodes detecting vital signs of a user and transmitting the detected vital signs to the signal capturing assembly; and
      a latching plate corresponding to a bottom surface of the case and being secured on the bottom surface of the case, wherein the case defines a through hole at an end of the case, the latching plate comprises a hook exposed from the through hole facing the receiving slot and latched to the first port.

2. The wearable electronic device of claim 1, wherein the signal capturing assembly comprises a base, a first cover, a second cover, a third cover, a first electrode, and a core module, the first cover, the second cover, the third cover being adapted to cover the base to form a receiving chamber to accommodate the core module, the first electrode is extended through the base and is electronically connected to the core module.

3. The wearable electronic device of claim 2, wherein the first cover is a second electrode electronically connected to the core module, the first cover defines a label configured for labeling a contact position of the first cover, when the label is pressed, a loop is formed between the first electrode and the second electrode so that the first electrode detects vital signs of an user and transmits the detected vital signs to the core module.

4. The wearable electronic device of claim 3, further comprising an accessory, wherein the accessory comprises a first connecting portion, a cable, and a second connecting portion; the first connecting portion and the second connecting portion being connected to two opposite ends of the cable, the first connecting portion is detachably connected to the signal capturing assembly, the second connecting portion is configured for connecting the signal capturing assembly to receive a charge or to communicatively couple to other electronic devices.

5. The wearable electronic device of claim 4, wherein the first cover defines the first port at an end of the first cover, the third cover defines a second port at an end of the third cover, the second port is electronically connected to the core module, the first port is connected to the holder, the second port is connected to one of the holder and the accessory.

6. The wearable electronic device of claim 5, wherein the holder further comprises a convertor arranged at another end of the case opposite to the through hole and configured for connecting to the second port of the signal capturing assembly; the convertor comprises two contacting rods protruding from the case configured for electrically connecting to the core module.

7. The wearable electronic device of claim 6, wherein the first connecting electrode comprises a first protrusion and a securing member, the first protrusion is secured on the case by the securing member; the second connecting electrode comprises a second protrusion, a positioning member, and a fastener, the second protrusion is arranged at an end of the positioning member, the fastener is extended through another end of the positioning member opposite to the protrusion and latches the positioning member to the case.

8. The wearable electronic device of claim 7, wherein the latching plate defines a first mounting hole and a second mounting hole corresponding to the first connecting electrode and the second connecting electrode, the first connecting electrode and the second connecting electrode are extended through the first mounting hole and the second mounting hole, respectively.

9. The wearable electronic device of claim 8, wherein the first connecting electrode and the second connecting electrode are electronically connected to the contacting rods, detect the vital signs of the user, and transmit the detected vital signs to the core module by the contacting rods.

10. The wearable electronic device of claim 4, wherein the accessory comprises a first connecting portion, a cable, and a second connecting portion, the first connecting portion and the second connecting portion are connected to two opposite ends of the cable, the first connecting portion comprises a rib protruded from an end of the first connecting portion configured for latching the first connecting portion to the second port, the first connecting portion is electronically connected to the core module by the second port.

11. A holder for a wearable electronic device, the holder comprising:
    a case defining a receiving slot;
    a first connecting electrode;
    a second connecting electrode, the first connecting electrode and the second connecting electrode protruding from a bottom surface of the case, the first connecting electrode and the second connecting electrode detecting vital signs of a user; and
    a latching plate corresponding to a bottom surface of the case and secured on the bottom surface of the case, the case defines a through hole at an end of the case, the latching plate comprising a hook exposed from the through hole facing the receiving slot.

12. The holder of claim 11, wherein the holder further comprises a convertor arranged at another end of the case opposite to the through hole; the convertor comprises two contacting rods protruding from the case.

13. The holder of claim 11, wherein the latching plate defines a first mounting hole and a second mounting hole corresponding to the first connecting electrode and the second connecting electrode, the first connecting electrode and the second connecting electrode are extended through the first mounting hole and the second mounting hole, respectively.

14. The holder of claim 11, wherein the first connecting electrode comprises a first protrusion and a securing member, the first protrusion is secured on the case by the securing member.

15. The holder of claim 14, wherein the second connecting electrode comprises a second protrusion, a positioning member, and a fastener, the second protrusion is arranged at an end of the positioning member, the fastener extends through another end of the positioning member opposite to the protrusion and latches the positioning member to the case.

16. The holder of claim 15, wherein the first connecting electrode and the second connecting electrode are electronically connected to the contacting rods.

17. A wearable electronic device comprising:
    a signal capturing assembly; and
    a holder, the holder comprising:
        a case defining a receiving slot configured for receiving the signal capturing assembly;
        a first connecting electrode; and
        a second connecting electrode, the first and second connecting electrodes protruding from a bottom surface of the case and being electronically connected to the signal capturing assembly, the first and second connecting electrodes detecting vital signs of a user and transmitting the detected vital signs to the signal capturing assembly;
    wherein the signal capturing assembly comprises a base, a first cover, a second cover, a third cover, a first electrode, and a core module, the first cover, the second cover, the third cover being adapted to cover the base to form a receiving chamber to accommodate the core module, the first electrode is extended through the base and is electronically connected to the core module;
    wherein the first cover defines a first port at an end of the first cover, the third cover defines a second port at an end of the third cover, the second port is electronically connected to the core module, the first port is connected to the holder, the second port is connected to one of the holder.

18. The wearable electronic device of claim 17, wherein the first cover is a second electrode electronically connected to the core module, the first cover defines a label configured for labeling a contact position of the first cover, when the label is pressed, a loop is formed between the first electrode and the second electrode so that the first electrode detects vital signs of an user and transmits the detected vital signs to the core module.

19. The wearable electronic device of claim 17, further comprising an accessory, wherein the accessory comprises a first connecting portion, a cable, and a second connecting portion; the first connecting portion and the second connecting portion being connected to two opposite ends of the cable, the first connecting portion is detachably connected to the signal capturing assembly, the second connecting portion is configured for connecting the signal capturing assembly to receive a charge or to communicatively couple to other electronic devices.

20. The wearable electronic device of claim 17, wherein the holder further comprises a convertor arranged at another end of the case opposite to the through hole and configured for connecting to the second port of the signal capturing assembly; the convertor comprises two contacting rods protruding from the case configured for electrically connecting to the core module.

21. The wearable electronic device of claim 17, wherein the holder further comprises a latching plate corresponding to a bottom surface of the case and being secured on the bottom surface of the case, the case defines a through hole at an end of the case, the latching plate comprises a hook exposed from the through hole facing the receiving slot and configured for latching to the first port.

* * * * *